US006818397B1

(12) United States Patent
Lee et al.

(10) Patent No.: US 6,818,397 B1
(45) Date of Patent: Nov. 16, 2004

(54) METHODS FOR DETECTING AND DIFFERENTIATING ENTEROVIRUSES AND THE PRIMERS AND PROBES THEREFOR

(75) Inventors: Kan-Hung Lee, Sanchung (TW); Chi-Horng Bair, Tucheng (TW); Yang-Yuan Tseng, Hsinchu (TW); Yih-Weng Wang, Tainan (TW); Shin-Hwan Wang, Hsinchu (TW)

(73) Assignee: Dr. Chip Biotechnology Incorporation, Taichung (TW)

( * ) Notice: Subject to any disclaimer, the term of this patent is extended or adjusted under 35 U.S.C. 154(b) by 82 days.

(21) Appl. No.: 09/724,678

(22) Filed: Nov. 28, 2000

(51) Int. Cl.[7] ............................ C12Q 1/68; C12P 19/34; C07H 21/04
(52) U.S. Cl. ........................ 435/6; 435/91.1; 435/91.2; 536/23.1; 536/24.3
(58) Field of Search ..................... 435/6, 91.1, 91.2, 435/287.2; 536/23.1, 24.3

(56) References Cited

U.S. PATENT DOCUMENTS 6,168,917 B1 * 1/2001 Kilpatrick ..................... 435/5

OTHER PUBLICATIONS

Shih et al; Journal of Virological Methods, vol. 111, pp. 55–60, 2003.*
Accession No. Af177911, Genbank, Sep. 1999.*
Accession No. AF136379, Genbank, Jun. 2000.*
Accession No. U22521, Genbank, Jan. 1997.*
Accession No. U55870, Genbank, May 1996.*
Accession No. Z78129, Genbank, Aug. 1997.*
Accession No. E30248, Genbank, Dec. 1999.*

* cited by examiner

Primary Examiner—Jehanne Sitton
(74) Attorney, Agent, or Firm—Kolisch Hartwell, P.C.

(57) ABSTRACT

The present invention discloses pairs of oligonucleotide primers for use in detecting the presence or absence of an enterovirus in a sample. Also disclosed are synthetic nucleotide sequences capable of specifically hybridizing to a sense strand of an enterovirus nucleic acid or a nucleic acid corresponding to the sense strand. The present invention provides a method of detecting the presence or absence of an enterovirus nucleic acid in a sample as well as a kit for detecting an enterovirus in a sample. The present invention particularly provides a method and a kit for detecting and differentiating enterovirus type 71 and/or coxsackievirus A16 in a sample.

4 Claims, 1 Drawing Sheet

Nucleotides 1-1560 of the genome of Eenterovirus type 71 BrCr (GenBank Accession No.: U22521)

```
   1 TTAAAACAGC TGTGGGTTGT CACCCACCCA CAGGGTCCAC TGGGCGCTAG TACACTGGTA
  61 TCTCGGTACC TTTGTACGCC TGTTTTATAC CCCTCCCTG ATTTGCAACT TAGAAGCAAC
                f1 (72-87)
 121 GCAAACCAGA TCAATAGTAG GTGTGACATA CCAGTCGCAT CTTGATCAAG CACTTCTGTA

181 TCCCCGGACC GAGTATCAAT AGACTGTGCA CACGGTTGAA GGAGAAAACG TCCGTTACCC
       f2 (167-187)
 241 GGCTAACTAC TTCGAGAAGC CTAGTAACGC CATTGAAGTT GCAGAGTGTT TCGCTCAGCA
              f3 (248-266)
 301 CTCCCCCCGT GTAGATCAGG TCGATGAGTC ACCGCATTCC CCACGGGCGA CCGTGGCGGT
 361 GGCTGCGTTG GCGGCCTGCC TATGGGGTAA CCCATAGGAC GCTCTAATAC GGACATGGCG
 421 TGAAGAGTCT ATTGAGCTAG TTAGTAGTCC TCCGGCCCCT GAATGCGGCT AATCCTAACT
         f5 (423-439)                                p1 (448-474)
 481 GCGGAGCACA TACCCTTAAT CCAAACGGCA GTGTGTCGTA ACGGGCAACT CTGCAGCGGA
                                                           p2 (514-546)
 541 ACCGACTACT TTGGGTGTCC GTGTTTCTTT TTATTCTTGT ATTGGCTGCT TATGGTGACA
           p3 (547-574)                           r2 (583-602)
 601 ATTAAAGAAT TGTTACCATA TAGCTATTGG ATTGGCCATC CAGTGTCAAA CAGAGCTATT
     r2 (583-602)                        r1 (627-645)
 661 GTATATCTCT TTGTTGGATT CACACCTCTC ACTCTTGAAA CGTTACACAC CCTCAATTAC
 721 ATTATACTGC TGAACACGAA GCGATGGGCT CCCAGGTCTC CACACAGCGA TCCGGCTCGC
 781 ATGAGAATTC CAACTCAGCC ACGGAAGGCT CCACTATAAA TTACACAACC ATTAATTACT
 841 ACAAAGACTC GTATGCTGCC ACTGCTGGAA AGCAAAGTCT CAAACAAGAT CCTGACAAGT
 901 TTGCGAACCC TGTGAAGGAC ATCTTTACTG AAATGGCAGC GCCCTTAAAG TCTCCCTCTG
 961 CTGAAGCATG TGGCTATAGC GACCGAGTGG CACAGCTTAC CATTGGAAAT TCCACCATTA
1021 CTACACAAGA AGCAGCAAAC ATAATAGTTG GGTATGGTGA GTGGCCTTCA TACTGCTCTG
1081 ATAATGATGC AACAGCGGTA GACAAACCTA CACGGCCTGA TGTCTCAGTA AATAGATTTT
1141 ACACGCTAGA CACTAAGCTA TGGGAGAAAT CATCCAAGGG GTGGTACTGG AAGTTCCCAG
                                                    f7 (1179-1198)
1201 ATGTACTGAC TGAAACCGGA GTTTTTGGTC AAATGCACA ATTTCACTAC TTATACCGTT
1261 CAGGGTTCTG CATCCACGTT CAATGTAACG CTAGCAAATT TCACCAAGGG GCGCTACTCG
1321 TTGCGGTATT GCCCGAGTAT GTCATTGGAA CAGTGGCAGG CGGCACAGGC ACAGAGAACA
                                                      16-1 (1343-1373)
1381 GTCACCCTCC TTATAAACAA ACCCAACCCG GCGCTGATGG ATTTGAATTA CAACATCCAT
         71-2 (1390-1419)/16-2 (1390-1419)
1441 ATGTTCTTGA TGCTGGAATT CCAATATCTC AGTTGACAGT GTGCCCTCAC CAGTGGATCA
             71-3 (1453-1481)                    r4 (1485-1504)
1501 ATTTACGAAC CAACAATTGT GCCACCATAA TAGTGCCATA CATGAACACA CTACCTTTTG
```

Figure 1

METHODS FOR DETECTING AND DIFFERENTIATING ENTEROVIRUSES AND THE PRIMERS AND PROBES THEREFOR

BACKGROUND OF THE INVENTION

Enteroviruses belong to the family Picornaviridae that represents a very large RNA-virus family with respect to the number of members but one of the smallest in terms of virion size and complexity. The virion of an enterovirus consists of a capsid of 60 subunits. Each subunit consisting of the four proteins (VP 1–VP4) arranged with icosahedral symmetry around a genome made up of a single strand of positive-sense RNA. Enteroviruses are transient inhabitants of the human alimentary tract and may be isolated from the lower intestine or the throat. Enteroviruses of human origin include polioviruses (serotypes 1 to 3), coxsackieviruses of groups A (CAV, serotypes 1 to 22 and 24) and B (CBV, serotypes 1 to 6), echoviruses (serotypes 1 to 9, 11 to 27 and 29 to 33) and enteroviruses (serotypes 68–71). Enteroviral infections in humans may result in a wide range of acute symptoms involving neurological, skin and mucosa, cardiac and muscular, ocular, respiratory and gastrointestinal conditions, as well as undifferentiated febrile illness, generalized diseases of infants and diabetes mellitus. Among the nonpolio enteroviruses, some unsubclassified serotypes have been particularly prevalent in some countries and areas during summer and early fall, e.g., enteroviruses 70 and 71. Enterovirus 71 has been isolated from patients with meningitis, encephalitis and paralysis resembling poliomyelitis. It continues to be one of the main causes of central nervous system diseases, sometimes fetal, around the world. Furthermore, the virus has caused outbreaks of human hand-foot-and-mouth disease in some areas, e.g., Japan, Sweden and Taiwan.

Common diagnoses of enteroviruses usually include recovery of the virus and serological tests. The recovery of the virus may includes isolation of the viruses from throat washings, throat swabs, stools, rectal swabs and sometimes cerebrospinal fluid (in aseptic meningitis cases). The isolated viral specimens are inoculated into tissue cultures or suckling mice (the latter is specific for coxsackieviruses) for propagation and identification. It takes one to two weeks to complete a run of viral recovery. In addition, intervention has to be made by qualified technicians.

Serologic tests are generally conducted by means of neutralization assays detecting the neutralizing antibodies specific to the infecting virus when they exist. For some echoviruses, hemagglutination-inhibition assays might show type-specific infections. Serum antibodies can also be detected or titrated by the immunofluorescence technique using infected cell cultures on coverslips as antigens. However, serologic tests are difficult to evaluate because of the multiplicity of serotypes, unless the antigen used has been isolated from a specific human or during an epidemic outbreak of typical clinic illness. In all of the serologic assays, skilled artisans are required to judge the cut-off values from the readouts. Also, a period of time and specialized techniques are usually required to prepare such an antigen used in those assays to reduce the incidence of heterotypic reactions or cross-reactions.

Neither the recovery of the virus nor the serologic tests provides a rapid diagnostic tool. Nevertheless, the acute syndromes associated with enteroviruses may progress fast, and in some cases may even become fatal in a couple of days. There is therefore a need for a method to rapidly detect enteroviruses with ease in practice.

SUMMARY OF THE INVENTION

The present invention relates to novel pairs of oligonucleotide primers for use in detecting the presence or absence of an enterovirus in a sample. Each pair of primers according to the present invention consists of a first primer and a second primer, which are useful in rapidly diagnosing the diseases or conditions associated with enteroviruses by nucleic acid amplification assays, such as polymerase chain reactions.

It is surprisingly found in the present invention that some nucleotide sequences correspond to the conserved portions in the nucleic acids of the enteroviruses. Therefore, the present invention further provides synthetic nucleotide sequences capable of specifically hybridizing to a sense strand of an enterovirus nucleic acid or a nucleic acid corresponding to the sense strand, such as the product of an amplification reaction with the sense strand as the template.

In another aspect, the present invention relates to a method of detecting the presence or absence of an enterovirus nucleic acid in a sample. The method according to the present invention comprises (a) contacting the sample with a pair of oligonucleotide primers according to the present invention in an amplification process; and (b) determining the presence or absence of an enterovirus by detecting the presence or absence of amplification products.

Preferably, in the method according to the present invention, the sample may be simultaneously contacted with a second pair of oligonucleotide primers according to the present invention in an amplification process in addition to the first pair of primers. The primers in the second pair are not the same as the primers in first pair. The primers in the second pair may have either the first or the second primer different from the corresponding primer in the first pair. Preferably, both primers in the second pair are different from the ones in the first pair. Furthermore, the sample may be simultaneously contacted with a third pair of the oligonucleotide primers according to the present invention in an amplification process, in addition to the first and second pairs of primers. In a similar manner, the third pair of primers is neither the same as the first pair of primers nor the second pair of primers.

In an alternative manner, the method according to the present invention may further comprise contacting the products of step (a) with a second pair of the oligonucleotide primers according to the present invention in an amplification process. The second pair of primers is chosen so as to be capable of being used to amplify a sequence in an amplification process that is equal to or within the sequence obtainable in the amplification process using the first pair of primers.

In another alternative of the method according to present invention, the amplification products detected in step (b) are further subjected to a specific hybridization with at least one synthetic nucleotide sequence according to the present invention.

In yet another aspect, the present invention relates to a method of detecting and differentiating enterovirus type 71 in a sample. The method comprises (a) contacting the sample with at least one pair of oligonucleotide primers according to the present invention in an amplification process; (b) determining the presence or absence of enterovirus type 71 by detecting for the presence or absence of amplification products; and (c) subjecting the amplification products detected to a specific hybridization with at least one synthetic nucleotide sequence comprising the sequence of SEQ ID NO: 12 or SEQ ID NO:13. Preferably, the amplification products detected are subjected to a specific hybridization with the synthetic nucleotide sequences comprising the sequences of SEQ ID NO:12 and SEQ ID NO:13.

In yet another aspect, the present invention relates to a method of detecting and differentiating coxsackievirus A16 in a sample. The method comprises contacting the sample with a pair of oligonucleotide primers according to the present invention in an amplification process; determining the presence or absence of coxsackievirus A16 by detecting the presence or absence of amplification products; and subjecting the amplification products detected to a specific hybridization with at least one synthetic nucleotide sequence comprising the sequence of SEQ ID NO: 14 or SEQ ID NO: 15. Preferably, the amplification products detected are subjected to a specific hybridization with the synthetic nucleotide sequences comprising the sequences of SEQ ID NO: 14 and SEQ ID NO: 15.

In yet another aspect, the present invention relates to a method of detecting and differentiating enterovirus type 71 and/or coxsackievirus A16 in a sample. The method comprises contacting the sample with a pair of oligonucleotide primers according to the present invention in an amplification process; determining the presence or absence of enterovirus type 71 and/or coxsackievirus A16 by detecting the presence or absence of amplification products; and subjecting the amplification products detected to a specific hybridization with at least a first synthetic nucleotide sequence comprising the sequence of SEQ ID NO:12 or SEQ ID NO: 13, and with at least a second synthetic nucleotide sequence comprising the sequence of SEQ ID NO: 14 or SEQ ID NO: 15. Preferably, the amplification products detected are subjected to a specific hybridization with the synthetic nucleotide sequences comprising the sequences of SEQ ID NO:12, SEQ ID NO:13, SEQ ID NO:14 and SEQ ID NO:15.

In yet another aspect, the present invention provides a kit for detecting an enterovirus in a sample, which comprises at least one pair of oligonucleotide primers according to the present invention. Preferably, the kit according to the present invention comprises more than one pair of primers according to the present invention. In an alternative of the present invention, the kit may further comprise at least one synthetic nucleotide sequence according to the present invention.

In yet another aspect, the present invention provides a kit for detecting and differentiating enterovirus type 71 in a sample, which comprises at least one pair of oligonucleotide primers according to the present invention and at least one synthetic nucleotide sequence comprising the sequence of SEQ ID NO: 12 or SEQ ID NO: 13. Preferably, the kit according to the present invention comprises more than one pair of primers according to the present invention. In a preferred embodiment of this invention, the kit comprises the synthetic nucleotide sequences comprising the sequences of SEQ ID NO: 12 and SEQ ID NO:13.

In yet another aspect, the present invention provides a kit for detecting and differentiating coxsackievirus A16 in a sample, which comprises at least one pair of oligonucleotide primers according to the present invention and at least one synthetic nucleotide sequence comprising the sequence of SEQ ID NO: 14 or SEQ ID NO: 15. Preferably, the kit according to the present invention comprises more than one pair of primers according to the present invention. In a preferred embodiment of this invention, the kit comprises the synthetic nucleotide sequences comprising the sequences of SEQ ID NO:14 and SEQ ID NO:15.

In yet another aspect, the present invention provides a kit for detecting and differentiating enterovirus type 71 and/or coxsackievirus A16 in a sample, which comprises at least one pair of oligonucleotide primers according to the present invention; and at least a first synthetic nucleotide sequence comprising the sequence of SEQ ID NO:12 or SEQ ID NO:13 and at least a second synthetic nucleotide sequence comprising the sequence of SEQ ID NO:14 or SEQ ID NO:15. Preferably, the kit according to the present invention comprises more than one pair of primers according to the present invention. In a preferred embodiment of this invention, the kit comprises the synthetic nucleotide sequences comprising the sequences of SEQ ID NOs:12–15.

BRIEF DESCRIPTION OF THE FIGURE

FIG. 1 is a schematic representation showing a portion of cDNA sequence corresponding to the genome of enterovirus type 71, where the cDNA sequence with the Accession No. U22521 was obtained from the database GenBank. The sequences in the boxes correspond to the primers and probes of the present invention that are identified with their codes designated by the inventors.

DETAILED DESCRIPTION OF THE PREFERRED EMBODIMENTS

The term "specifically hybridizing" or "specific hybridization" means complementary hybridization between an oligonucleotide and a target sequence. The term "specific" or "specifically" refers to the specificity shown by the complementary hybridization, which allows for minor mismatches between the oligonucleotide and the sequence that may not jeopardize the annealing for detection of hybridization signals.

The term "sample" means a sample comprising any biological material containing nucleic acids. Preferably the term "sample" refers to a biological sample including whole blood, serum, urine, saliva, cerebrospinal fluid, semen, tears, throat swab, rectal swab, feces and the like.

The term "amplification process" means an assay or method for amplifying a nucleic acid sequence. For instance, the "amplification process" includes a polymerase chain reaction (PCR) assay, a ligase chain reaction (LCR) assay, Qβ-replicase amplification, in vitro transcription, in vitro retro-transcription and self-sustained sequence replication.

The term "highly stringent conditions" means the conditions of hybridization that are chosen to be about 5° C. lower than the thermal melting point ($T_m$) for the specific sequence at a defined ionic strength and pH. The thermal melting point is the temperature (under the defined ionic strength and pH) at which 50% of the target sequence hybridizes to a perfectly matched probe. Typically, highly stringent conditions will be those in which the salt concentration is about 0.2 molar at pH 7 and the temperature is at least above 60° C.

The codes for bases as used herein cover those representing naturally occurring purines and pyrimidines found in native DNA molecules (i.e., A, G, T and C), as well as those for mixed bases as usually recognized by persons skilled in the art for syntheses of oligonucleotides (such as R, Y, S, H). With respect to the codes used in the present specification, A (or a) represents adenine, G (or g) represents guanine, T (or t) represents thymine, C (or c) represents cytosine, R (or r) represents either adenine or guanine, Y (or y) represents either cytosine or thymine, S (or s) represents either guanine or cytosine, and H (or h) represents any of adenine, thymine and cytosine.

The present invention is useful for the detection of nucleic acids derived from enteroviruses. The present invention provides a rapid and sensitive method to detect the presence or absence of the nucleic acids derived from enteroviruses. In a preferred embodiment of the present invention, the method according to the present invention is an assay on the basis of polymerase chain reactions (PCR). In another aspect, the present invention provides very specific pairs of PCR primers that can be used to detect and/or identify particular serotypes of enteroviruses, such as enterovirus type 71 and coxsackievirus A16. In yet another aspect, the present invention provides specific nucleotide sequences, which are capable of specifically hybridizing with the nucleic acid fragments obtainable from the amplification process using the pairs of primers according to the present invention.

A number of amplification processes may be used, but a PCR-based process is preferred. The PCR process is well known in the art and is thus only briefly described herein. For a review of PCR methods and protocols, see, e.g., U.S. Pat. Nos. 4,683,195 and 4,683,202; 4,965,188; and Innis, et al., eds. PCR Protocols. "A Guide to Methods and Application" (Academic Press, Inc., San Diego, Calif. 1990). PCR reagents and protocols are also commercially available.

Because enteroviruses are RNA viruses, the first step in the amplification is the synthesis of a DNA copy (cDNA) of the region to be amplified. Reverse transcription can be carried out as a separate step, or in a homogeneous reverse transcription-polymerase chain reaction (RT-PCR), a modification of the polymerase chain reaction for amplifying RNA. Methods suitable for PCR amplification of enterovirus nucleic acids are described in Romero and Rotbart in "Diagnostic Molecular Biology: Principles and Applications" pp.401–406, Persing et al. eds., (Mayo Foundation, Rochester, Minn. 1993); Rotbart et al. U.S. Pat. No. 5,075, 212 and Egger et al., J. Clin. Microbiol. 33:1442–1447 (1995)).

The present invention provides novel pairs of oligonucleotide primers for use in detecting the presence or absence of enterovirus in a sample. Each pair of primers according to the present invention consists of a first primer and a second primer which are useful in diagnosing rapidly the diseases or conditions associated with enteroviruses by nucleic acid amplification assays, such as polymerase chain reactions. The primers according to the present invention target the sense or antisense strands of nucleotide sequences that correspond to particular conserved regions. Particular combinations of a primer pair or groups of primer pairs yield a matrix of amplification products that is used to detect enteroviruses present in a sample. In the preferred combinations of the present invention, the first primer comprises a sequence selected from the group consisting of

| f1: | TTGTRCGCCTGTTTTA | (SEQ ID NO: 1), |
| f2: | CAAGCACTTCTGTHHCCCCGG | (SEQ ID NO: 2), |
| f3: | TACTTCGAGAARCCYAGTA | (SEQ ID NO: 3), |

-continued

| f5: | AAGAGYCTATTGAGCTA | (SEQ ID NO: 4) and |
| f7: | GGI TGG TRS TGG AAR TTI CC | (SEQ ID NO: 5). |

The second primer comprises a sequence selected from the group consisting of

| r1: | CACYGGATGGCCAATCCAA | (SEQ ID NO: 6), |
| r2: | ATTGTCACCATAAGCAGCCA | (SEQ ID NO: 7), and |
| r4: | AR RTT IAT CCA YTG RTG IGG | (SEQ ID NO: 8). |

The sequences of the primers of the present invention correspond to the known enteroviral cDNA sequences in the boxes as shown in FIG. 1. When designing the primers, base modifications were made to the corresponding viral cDNA sequences so as to enhance the efficiency of primer annealing and broaden the spectrum of sequence diversity that the primers can be employed to detect.

The primers comprising the sequences of SEQ ID NOs: 5 and 8 according to the present invention correspond to the coding regions of the enteroviral genome. The primers corresponding to the coding regions of the enteroviral genome are intended to cover those primers comprising the degenerate sequences in relation to the sequences of SEQ ID NOs: 5 and 8. The sequences of SEQ ID NOs: 5 and 8 above are schematically depicted in relevant triplets according to the codons to which the sequences correspond.

In the present invention, a more preferred combination comprises one or more of the following primer pairs:

| f1(SEQ ID NO: 1)/r1(SEQ ID NO: 6); | f2(SEQ ID NO: 2)/r1(SEQ ID NO: 6); |
| f3(SEQ ID NO: 3)/r1(SEQ ID NO: 6); | f5(SEQ ID NO: 4)/r1(SEQ ID NO: 6); |
| f1(SEQ ID NO: 1)/r2(SEQ ID NO: 7); | f2(SEQ ID NO: 2)/r2(SEQ ID NO: 7); |
| f3(SEQ ID NO: 3)/r2(SEQ ID NO: 7); | f5(SEQ ID NO: 4)/r2(SEQ ID NO: 7); and |
| f7(SEQ ID NO: 5)/r2(SEQ ID NO: 7). | |

In a preferred aspect of the present invention, the pair of primers f7(SEQ ID NO: 5)/r4(SEQ ID NO: 8) are particularly suited to the detection of enterovirus type 71 (EV71) and coxasackievirus A16 (Cox A 16) in an amplification process.

In view of FIG. 1, persons skilled in the art can understand the way to choose at least a pair of primers of the present invention that are suitable for detecting and/or amplifying a desired fragment(s) in the enteroviral genome, and accordingly determine the pair(s) of primers with ease. As shown in FIG. 1, the second primer should comprise the sequence of SEQ ID NO: 8 or a degenerate sequence thereof when the first primer comprises the sequence of SEQ ID NO: 5 or a degenerate sequence thereof.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids, in particular ribonucleic acids, from biological samples are known in the art. Alternatively, if the sample is fairly readily disruptable, the nucleic acid need not be purified prior to amplification by the PCR technique, i.e., if the sample is comprised of cells, particularly peripheral blood lymphocytes or monocytes, lysis and dispersion of the intracellular components may be accomplished merely by suspending the cells in a hypotonic buffer.

The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In the preferred embodiment of the PCR process, strand separation is achieved by heating the reaction to a sufficiently high temperature for a sufficient time to cause the denaturation of the duplex but not to cause an irreversible denaturation of the polymerase (see U.S. Pat. No. 4,965, 188). Template-dependent extension of primers in PCR is catalyzed by a polymerizing agent in the presence of adequate amounts of four deoxyribonucleoside triphosphates (typically dATP, dGTP, dCTP, and dTTP) in a reaction medium comprised of the appropriate salts, metal cations, and pH buffering system. Suitable polymerizing agents are enzymes known to catalyze template-dependent DNA synthesis. In the present invention, the initial template for primer extension is typically RNA. Reverse transcriptases (RTs) suitable for synthesizing a cDNA from the RNA template are well known.

PCR is most usually carried out as an automated process with a thermostable enzyme. In this process, the temperature of the reaction mixture is cycled through a denaturing region, a primer annealing region and an extension reaction region automatically.

As described above, a preferred embodiment of the invention incorporates RT-PCR amplification. A person skilled in the art will recognize, however, that amplification of target sequences in a sample may be accomplished by any known method, such as ligase chain reaction (LCR), Qβ-replicase amplification, in vitro transcription, and self-sustained sequence replication, each of which provides sufficient amplification.

The size of the amplified fragments (the "amplification products") produced by the methods of the present invention is typically sufficient to determine the presence or absence of enteroviruses. Thus, in some embodiments of the invention, size fractionation (e.g., gel electrophoresis) of the amplified fragments produced in a given sample can be used to determine the presence or absence of enteroviruses in the sample. This is typically carried out by amplifying a control containing known nucleic acids with the same primers used to amplify the samples of interest. After running the amplified sequences in an agarose gel and labeling with ethidium bromide according to conventionally known techniques (see, Sambrook et al.), the pattern of bands in the sample and control are compared. The presence of to different or additional bands in the sample as compared to the control group is an indication of the presence of enteroviruses.

To ascertain the accuracy of results of PCR amplifications, more than one pair of primers can be employed in an amplification process. In the method according to the present invention, pairs of primers that are different with respect to each other may be employed simultaneously or sequentially. In the case where more than one pair of primers according to the present invention is employed simultaneously in an amplification process, a pair of primers may differ from another pair of primers in either the first primer or the second primer, or both of the first and second primers. In another case, if two pairs of primers according to the present invention are employed sequentially in an amplification process, the second pair of primers is capable of being used to amplify a sequence equal to or within the sequence that is supposedly obtainable in the amplification process using the first pair of primers. According to FIG. 1, a practitioner can carry out the methods of the present invention by determining with ease more than one pair of primers that is to be employed simultaneously or sequentially.

Alternatively, the amplification products of the present invention can be detected using oligonucleotide probes specific to the target nucleic acids. The probes are usually selected from the regions of the genome of the enterovirus that are specific to one or the other.

Sequence-specific probe hybridization is a well-known method of detecting desired nucleic acids in a sample. Under sufficiently stringent hybridization conditions, the probes hybridize specifically only to substantially complementary sequences. The stringency of the hybridization conditions can be relaxed to tolerate varying amounts of sequence mismatch. Detection of the amplified product utilizes this sequence-specific hybridization to insure detection of only the correct amplified target, thereby decreasing the chance of a false positive caused by the presence of homologous sequences from related organisms or other contaminating sequences.

It is surprisingly found in the present invention that certain nucleotide sequences correspond to the conserved portions in the nucleic acids of the enteroviruses. Therefore, the present invention further provides the synthetic nucleotide sequences capable of specifically hybridizing to a sense strand of an enterovirus nucleic acid or a nucleic acid corresponding to the sense strand (such as the product of an amplification reaction using the sense strand as the template). Those synthetic nucleotide sequences are useful as probes in hybridization assays for enteroviruses. Preferably, the synthetic nucleotide sequences selected from the group consisting of

| | | |
|---|---|---|
| p1: | TCCTCCGGCCCCTGAATGCGGCTAATC | (SEQ ID NO: 9), |
| p2: | TGTCGTAACGSGCAASTCYGYRGCGGAACCGAC | (SEQ ID NO: 10), |
| p3: | TACTTTGGGTGTCCGTGTTTCHTTTTAT | (SEQ ID NO: 11), |
| 71-2: | C TTA TAA GCA GAC TCA ACC CGG TGC TGA TG | (SEQ ID NO: 12), |

| | | |
|---|---|---|
| 71-3: | TGG CAT TCC AAT ATC ACA ATT AAC AGT G | (SEQ ID NO: 13), |
| 16-1: | CTC GGC ACT ATC GCA GGA GGG ACC GGG AAT | (SEQ ID NO: 14) and |
| 16-2: | C CTA CGC CAC TAC ACA GCC TGG TCA GGT TG | (SEQ ID NO: 15). |

The synthetic nucleotide sequences of the present invention correspond to the known enteroviral cDNA sequences in the boxes as shown in FIG. 1. The nucleotide sequences comprising the sequences of SEQ ID NOs:12–15 according to the present invention correspond to the coding regions of the enteroviral genome. The nucleotide sequences corresponding to the coding regions of the enteroviral genome are intended to cover those comprising the degenerate sequences in relation to the sequences of SEQ ID NOs: 12–15. The sequences of SEQ ID NOs:12–15 above are schematically depicted in relevant triplets according to the codons to which the sequences correspond.

In view of FIG. 1, persons skilled in the art can understand the way to choose at least a nucleotide sequence of the present invention for use as a probe in a hybridization assay using the primers of the present invention, and accordingly determine the probe(s) with ease. As shown in FIG. 1, the nucleotide sequence should not comprise a sequence of any of SEQ ID Nos:12–15 nor a degenerate sequence thereof when the second primer comprising the sequence of SEQ ID NO:8 or a degenerate sequence thereof is not employed for amplification. Moreover, the nucleotide sequence should not comprise a sequence of any of SEQ ID Nos:9–11 when the first primer comprising the sequence of SEQ ID NO:5 or a degenerate sequence thereof is not employed for amplification.

Several hybridization modes are well known in the art, including but not limited to, solution phase, solid phase, mixed phase or in situ hybridization assays. In solution (or liquid) phase hybridizations, both the target nucleic acid and the probe or primer are free to interact in the reaction mixture. In solid phase hybridization assays, either the target or probes are linked to a solid support where they are available for hybridization with complementary nucleic acids in solution. Exemplary solid phase modes include Southern hybridizations, dot blots and the like. The detection for hybridization may be carried out on a solid support such as a microtiter plate, a membrane (e.g. nitrocellulose) or a microsphere (bead) or a chip and any feasible hybridization buffer system.

The hybridization complexes are detected according to well-known techniques, and such detection is not a critical aspect of the present invention. Nucleic acid probes capable of specifically hybridizing to a target can be labeled by any one of several methods typically used to detect the presence of hybridized nucleic acids.

A common method of detection is the use of autoradiography using probes labeled with $^{3}H$, $^{125}I$, $^{35}S$, $^{14}C$, $^{32}p$ or the like. The choice of radioactive isotope depends on research preferences due to ease of synthesis, stability and half-life of the selected isotopes. The detection of hybridization signals may be conducted on a solid support, such as a microtiter plate, a membrane (e.g. nitrocellulose), a microsphere (bead) or a chip, as well as any feasible hybridization buffer system.

Other labels include ligands which bind to antiligands or antibodies labeled with fluorophores, chemilluminescent agents and enzymes. Alternatively, probes can be conjugated directly with labels such as fluorophores, chemiluminescent agents or enzymes. The choice of label depends on sensitivity required, ease of conjugation with the probe, stability requirements and available instrumentation.

The probes and primers of the invention can be synthesized and labeled using conventionally known techniques. Oligonucleotides for use as probes and primers may be chemically synthesized according to the solid phase phosphoramidite triester method first described by Beaucage, S. L. and Caruthers, M. H., 1981, Tetrahedron Letts., 22(20):1859–1862 using an automated synthesizer, as described in Needham-VanDevanter, D. R., et al. 1984, Nucleic Acids Res., 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

The above described primers and assays are used to detect enteroviruses in a sample, to diagnose enteroviral diseases and medical conditions and to correlate (or disprove a correlation between) specific symptoms or combinations of symptoms with the presence of a particular enterovirus. Diagnostic applications are supplemented and confirmed by an examination of the medical history and profile of the individual tested. Enteroviral diseases, medical conditions and symptoms that are diagnosed by the methods of the invention encompass all diseases, medical conditions and symptoms reported to be associated with enteroviruses here and in the scientific literature, specifically including aseptic meningitis, enteroviral diabetes mellitus, enteroviral conjunctivitis, acute flaccid paralysis, acute benign pericarditis, exanthema, enanthema, dilated cardiomyopathy, foot and mouth disease, chronic fatigue syndrome, febrile illnesses and upper respiratory tract infections. The detection of enteroviral infections and their correlation with medical conditions will make possible vaccines and methods of treatment.

The present invention also provides kits, multicontainer units comprising components useful for practicing the present method. A useful kit can contain probes for detecting the desired target nucleic acid. In some cases, the probes may be fixed to an appropriate support membrane. The kit will also contain primers provided in the present invention. Other optional components of the kit include, for example, reverse-transcriptase or polymerase, the substrate nucleoside triphosphates, means used to label (for example, an avidin-enzyme conjugate and enzyme substrate and chromogen if the label is biotin) and the appropriate buffers for reverse transcription, PCR, or hybridization reactions. In addition to the above components, the kit can also contain instructions for carrying out the method of the present invention.

All of the literature and publications as recited in the context of the present disclosure are incorporated herein by reference.

Other features and advantages of the present invention will be apparent from the following description of the preferred embodiments and from the claims.

EXAMPLES

The following examples illustrate various aspects of the present invention but do not limit the claims in any manner whatsoever.

Example 1

Detection of Enteroviruses

1.1. Viruses

59 Enteroviral specimens (see Table 1) used were either isolated from samples collected in clinic or obtained from the American Type Culture Collection (ATCC). The enteroviruses were identified by neutralization assays using pools of immuosera, followed by the confirmation of their serotypes with monotypic neutralizing polyclonal antibodies. As the results indicated, the 59 specimens covers a variety of enteroviral serotypes (see Table 1). Viruses were propagated in MRC5 cell monolayer cultures.

1.2. RNA Extraction

Viral RNAs were obtained by the isolation of total nucleic acids from cell pellets of the infected monolayer cell cultures. Approximately 4–6×10$^6$ cells per ml were lysed in a lysis buffer (50 mM NaCl, 20 mM Tris HCl (pH 7.5), 50 mM EDTA, 1% sodium dodecyl sulfate), extracted three times with phenol-chloroform and once with chloroform and then precipitated from 2.5 M ammonium acetate with ethanol. Nucleic acid pellets were washed with 75% ethanol, dried and suspended in 100 µl of sterile distilled water. RNA preparations were stored at −80° C.

1.3. PCR Amplification Assays

The first step of the amplification was the synthesis of a DNA copy (cDNA) of the portion of the enteroviral RNA genome to be amplified (i.e., the reverse transcription step). Reverse transcription by polymerase chain reactions were carried out in 20 µl of reaction mixtures (1 µl of each of total RNA in 20 mM Tris-HCl (pH 8.4), 50 mM KCl, 5 mM MgCl$_2$, 10 mM DTT, 0.5 mM of each of dATP, dCTP, dGTP and dTTP, and 50 ng of random hexamers). Samples were incubated at 65° C. for 5 minutes, then placed on ice for at least 1 minute. 50 units of reverse transcriptase were added and the mixtures were incubated at 42° C. for 50 minutes. The reactions were ceased by incubation at 70° C. for 15 minutes. The obtained cDNA products were stored at −20° C.

DNA amplifications by PCR were carried out in 25 µl reaction mixtures [12 µl of cDNA, 20 mM Tris-HCl (pH 8.0), 0.1 mM EDTA, 1 mM DTT, 1.0% triton X-100, 50% glycerol, 1.5 mM MgCl$_2$, 150 uM of each of dATP, dCTP, dGTP and dTTP, 10 pmol of each primer and 2.5 U of Taq DNA polymerase]. The primer pairs used in the amplification reactions were those comprising the sequences of f1(SEQ ID NO: 1)/r1(SEQ ID NO: 6), f2(SEQ ID NO: 2)/r1(SEQ ID NO: 6),
f3(SEQ ID NO: 3)/r1(SEQ ID NO: 6), f5(SEQ ID NO: 4)/r1(SEQ ID NO: 6),
f1(SEQ ID NO: 1)/r2(SEQ ID NO: 7), f2(SEQ ID NO: 2)/r2(SEQ ID NO: 7),
f3(SEQ ID NO: 3)/r2(SEQ ID NO: 7) and f5(SEQ ID NO: 4)/r2(SEQ ID NO: 7).

Primers r1 and r2 were labeled with biotin at 5' end for the following detection procedure. Each amplification reaction was conducted for 40 thermal cycles (denaturation for 4 minutes at 94° C., primer annealing for 1 minute at 55° C., and elongation for 1 minute at 72° C.).

1.4. Separation of DNA Products

Aliquots of PCR products (10 µl for each) were subjected to electrophoresis on 1.5% agarose gel in 0.5×TBE buffer (0.045M Tris-borate, 0.001M EDTA) for 30 minutes at 100 volts. After electrophoresis, the gel was stained with ethidium bromide and observed under UV illumination. The amplifications of all viral specimens using the primers of the present invention showed positive results by observation under UV. The data of the PCR amplification using the primer pair f5/r1 for the 59 viral specimens are illustrated in Table 1.

TABLE 1

| Serotype | Case No. | Case No. showing positive PCR results |
|---|---|---|
| EV 71 | 17 | 17 |
| CA 7 | 2 | 2 |
| CA 9 | 1 | 1 |
| CA 10 | 1 | 1 |
| CA 11 | 1 | 1 |
| CA 16 | 14 | 14 |
| CA 24 | 1 | 1 |
| CB 1 | 1 | 1 |
| CB 2 | 1 | 1 |
| CB 3 | 1 | 1 |
| CB 4 | 1 | 1 |
| CB 5 | 5 | 5 |
| CB 6 | 1 | 1 |
| Echo 1 | 1 | 1 |
| Echo 2 | 1 | 1 |
| Echo 3 | 1 | 1 |
| Echo 4 | 1 | 1 |
| Echo 5 | 1 | 1 |
| Echo 6 | 1 | 1 |
| Echo 7 | 3 | 3 |
| Echo 9 | 1 | 1 |
| Echo 11 | 1 | 1 |
| Echo 14 | 1 | 1 |
| Total | 59 | 59 |

1.5. Hybridization Analysis

Three enterovirus-specific probes (p1, p2 and p3) were used to detect the amplified DNA fragments, which comprise the sequences of SEQ ID NO: 9, SEQ ID NO: 10 and SEQ ID NO: 11, respectively.

The probes were denatured by heat (95° C., 5 minutes) and quickly quenching on ice for 2 minutes, followed by immobilization of those probes (10 µM for each) on nylon membranes (available from Boehringer Manngeim). The three probes (one µl for each) were applied and exposed to a source of ultraviolet irradiation (254 nm, 0.15 J/cm$^2$).

Biotin-labeled PCR products (8 µl for each) were denatured by heating at 95° C. for 5 minutes and then quenched on ice for 2 minutes, and were added into a hybridization solution [5×standard saline citrate (SSC), 0.1% (w/v) N-lauroylsarcosine, 0.1% (w/v) sodium dodecyl sulfate (SDS), 1×blocking buffer (Boehringer Manngeim) (20 ml/100 cm$^2$)]. The hybridization solution containing the PCR products was then incubated with the nylon membranes bound with labeled probes. After incubation at 50° C. for 1 hour, the membranes were washed 5 times at room temperature by a washing buffer (2×SSC of 0.1% SDS), followed by the addition of streptavidin alkaline phosphatase (2 µl/20 ml 1×blocking solution). The membranes were placed at room temperature for 30 minutes and then washed five times at room temperature with a maleic acid buffer (0.1 M maleic acid, 0.15 M NaCl, pH 7.5). The membranes were then equilibrated in a detection buffer (0.1 M Tris-HCl; 0.1

M NaCl; 50 mM MgCl$_2$, pH 9.5) for 5 minutes and incubated with a freshly prepared color-substrate solution (45 µl NBT solution mixed with 35 µl X-phosphate solution, and the detection buffer was added to 10 ml) in the dark for 10 minutes. Finally the membrane were washed with 1×TE buffer solution to stop reaction and air-dried at room temperature. The hybridization signals were detected and recorded. The results are shown in Table 2.

TABLE 2

| Serotype | Number of test cases | Number of cases showing detectable hybridization signals | | |
|---|---|---|---|---|
| | | P1 | P2 | P3 |
| CA 16 | 6 | 6 | 6 | 6 |
| CA 21 | 1 | 1 | 1 | 1 |
| CA 24 | 1 | 1 | 1 | 1 |
| CB 1 | 1 | 1 | 1 | 1 |
| CB 2 | 2 | 2 | 2 | 2 |
| CB 3 | 1 | 1 | 1 | 1 |
| CB 4 | 1 | 1 | 1 | 1 |
| CB 5 | 1 | 1 | 1 | 1 |
| CB 6 | 1 | 1 | 1 | 1 |
| Echo 3 | 3 | 3 | 3 | 3 |
| Echo 5 | 1 | 1 | 1 | 1 |
| Echo 6 | 1 | 1 | 1 | 1 |
| Echo 9 | 2 | 2 | 2 | 2 |
| Echo 11 | 3 | 3 | 3 | 3 |
| Echo 14 | 1 | 1 | 1 | 1 |
| Echo 21 | 3 | 3 | 3 | 3 |
| Echo 24 | 1 | 1 | 1 | 1 |
| Echo 30 | 2 | 2 | 2 | 2 |
| Echo 31 | 2 | 2 | 2 | 2 |
| EV 71 | 7 | 7 | 7 | 7 |
| Polio 1 | 2 | 2 | 2 | 2 |
| Polio 2 | 2 | 2 | 2 | 2 |
| Polio 3 | 2 | 2 | 2 | 2 |

Example 2

Detection and Differentiation of Enterovirus Type 71 (EV71) and Coxsackievirus A16 (Cox A16)

2.1. PCR Amplificaiton Assay:

RNA extraction and reverse transcription were carried out in the same conditions described in Example 1. PCR primers used in the assay were those comprising the sequences of f7(SEQ ID NO: 5)1 r4(SEQ ID NO: 8).

The PCR reaction mixtures and thermal cycling conditions were adjusted as described in Example 1.

2.2. Hybridization Assay:

The probes used for the detection of EV 71 were those comprising the sequences of SEQ ID NO: 12 (71-2) and SEQ ID NO: 13 (71-3). The probes used in the Cox A16 detection assay were those comprising the sequences of SEQ ID NO: 14 (16-1) and SEQ ID NO: 15 (16-2). Hybridization assays were performed in the conditions described in Example 1.

Results showed that the method of the present invention using primer pair f7/r4 and the probes 71-2 and 71-3 could specifically detect and differentiate EV71 and non-EV71 enteroviruses. Results also showed that the method of the present invention using the primer pair f7/r4 and the probes 16-1 and 16-2 could specifically detect and differentiate Cox A 16 and non-Cox A16 enteroviruses.

Example 3

Kit for Detecting and Differentiating EV71, Cox A16, non-EV71 Enteroviruses and non-Cox A16 Enteroviruses EV71 and Cox A16 were subjected to a detection assay simultaneously using a kit of the present invention. The kit provides materials and protocols to enable a practitioner to conduct a multiplex PCR assay. Viral RNA extraction and reverse transcription were carried out as described in Example 1. The multiplex PCR were carried out in 25 µl reaction mixtures (each containing 12 µl of cDNA, 50 mM Tris-HCl (pH 8.3), 70 mM KCl, 2.5 mM MgCl$_2$, 200 µM of each of dATP, dCTP, dGTP and dTTP, 10 pmol of the primers f5/r1, 20 pmol of the primers 17/r4 and 3 U of Taq DNA polymerase). Amplifications were conducted in 40 thermal cycles consisting of denaturation for 4 minute at 94° C., primer annealing for 1 minute at 55° C., and elongation for 1 minute at 72° C. After the multiplex PCR amplifications, the PCR products obtained were incubated with a membrane immobilized with the probes (p1, p2 and p3 for enteroviruses, 71-2 and 71-3 specific for EV71, and 16-1 and 16-2 specific for Cox A16). All conditions of the hybridization assay were the same as those described in Example 1. Results show that the kit providing a system comprising multiplex PCR and multiplex hybridization detection could both detect and differentiate EV71, Cox A16, non-EV71 enteroviruses and non-Cox A16 enteroviruses. The data of the hybridization assay using different probes of the present invention are illustrated in Table 3.

TABLE 3

| Serotype of enterovirus | Number of test cases | Number of cases showing detectable hybridization signals probes of the present invention | | | | | | |
|---|---|---|---|---|---|---|---|---|
| | | p1 | p2 | p3 | 71-2 | 71-3 | 16-1 | 16-2 |
| CA 16 | 6 | 6 | 6 | 6 | 0 | 0 | 6 | 6 |
| CA 21 | 1 | 1 | 1 | 1 | 0 | 0 | 0 | 0 |
| CA 24 | 1 | 1 | 1 | 1 | 0 | 0 | 0 | 0 |
| CB 1 | 1 | 1 | 1 | 1 | 0 | 0 | 0 | 0 |
| CB 2 | 2 | 2 | 2 | 2 | 0 | 0 | 0 | 0 |
| CB 3 | 1 | 1 | 1 | 1 | 0 | 0 | 0 | 0 |
| CB 4 | 1 | 1 | 1 | 1 | 0 | 0 | 0 | 0 |
| CB 5 | 1 | 1 | 1 | 1 | 0 | 0 | 0 | 0 |
| CB 6 | 1 | 1 | 1 | 1 | 0 | 0 | 0 | 0 |
| Echo 3 | 3 | 3 | 3 | 3 | 0 | 0 | 0 | 0 |
| Echo 5 | 1 | 1 | 1 | 1 | 0 | 0 | 0 | 0 |
| Echo 6 | 1 | 1 | 1 | 1 | 0 | 0 | 0 | 0 |
| Echo 9 | 2 | 2 | 2 | 2 | 0 | 0 | 0 | 0 |
| Echo 11 | 3 | 3 | 3 | 3 | 0 | 0 | 0 | 0 |
| Echo 14 | 1 | 1 | 1 | 1 | 0 | 0 | 0 | 0 |
| Echo 21 | 3 | 3 | 3 | 3 | 0 | 0 | 0 | 0 |
| Echo 24 | 1 | 1 | 1 | 1 | 0 | 0 | 0 | 0 |
| Echo 30 | 2 | 2 | 2 | 2 | 0 | 0 | 0 | 0 |
| Echo 31 | 2 | 2 | 2 | 2 | 0 | 0 | 0 | 0 |
| EV 71 | 7 | 7 | 7 | 7 | 7 | 7 | 0 | 0 |
| Polio 1 | 2 | 2 | 2 | 2 | 0 | 0 | 0 | 0 |
| Polio 2 | 2 | 2 | 2 | 2 | 0 | 0 | 0 | 0 |
| Polio 3 | 2 | 2 | 2 | 2 | 0 | 0 | 0 | 0 |

Various modifications and variations of the present invention will be apparent to those persons skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A kit for detecting and differentiating an enterovirus in a sample, comprising at least one pair of oligonucleotide primers for nucleic acid amplification, wherein a first primer of said pair consists of a sequence of any of:
SEQ ID NO: 1: TTGTRCGCCTGTTTTA,
SEQ ID NO: 2: CAAGCACTTCTGTHHCCCCGG,
SEQ ID NO: 3: TACTTCGAGAARCCYAGTA,
SEQ ID NO: 4: AAGAGYCTATTGAGCTA, or
SEQ ID NO: 5: GGITGGTRSTGGAARTTICC, or a degenerate sequence of SEQ ID No: 5; and
a second primer of said pair consists of a sequence of any of:
SEQ ID NO: 6: CACYGGATGGCCAATCCAA,
SEQ ID NO: 7: ATTGTCACCATAAGCAGCCA, or
SEQ ID NO: 8: ARRTTIATCCAYTGRTGIGG, or a degenerate sequence of SEQ ID No: 8,
provided that the second primer consists of the sequence of SEQ ID NO: 8 or a degenerate sequence of SEQ ID NO: 8 when the first primer consists of the sequence of SEQ ID NO: 5 or a degenerate sequence of SEQ ID NO: 5; and
at least one synthetic nucleotide sequence fixed on a solid substrate for nucleic acid hybridization with nucleic acids obtained from the amplification, wherein the synthetic nucleotide comprises any sequence selected from the group consisting of:
SEQ ID NO: 9: TCCTCCGGCCCCTGAATGCGGCTAATC,
SEQ ID NO: 10: TGTCGTAACGSGCAASTCYGYRGCGGAACC GAC,
SEQ ID NO: 11: TACTTTGGGTGTCCGTGTTTCHTTTTAT,
SEQ ID NO: 12: CTTATAAGCAGACTCAACCCGGTGCTGATG,
SEQ ID NO: 13: TGGCATTCCAATATCACAATTAACAGTG,
SEQ ID NO: 14: CTCGGCACTATCGCAGGAGGGACCGGGAAT or
SEQ ID NO: 15: CCTACGCCACTACACAGCCTGGTCAGGTTG, or a degenerate sequence of any of SEQ ID Nos.: 12–15.

2. A kit for detecting and differentiating an enterovirus in a sample, comprising at least one synthetic nucleotide sequence fixed on a solid substrate for nucleic acid hybridization with nucleic acids in the sample, wherein the synthetic nucleotide sequences consists of any sequence selected from the group consisting of
SEQ ID NO: 9: TCCTCCGGCCCCTGAATGCGGCTAATC,
SEQ ID NO: 10: TGTCGTAACGSGCAASTCYGYRGCGGAACC GAC,
SEQ ID NO: 11: TACTTTGGGTGTCCGTGTTTCHTTTTAT,
SEQ ID NO: 12: CTTATAAGCAGACTCAACCCGGTGCTGATG,
SEQ ID NO: 13: TGGCATTCCAATATCACAATTAACAGTG,
SEQ ID NO: 14: CTCGGCACTATCGCAGGAGGGACCGGGAAT or
SEQ ID NO: 15: CCTACGCCACTACACAGCCTGGTCAGGTTG, or a degenerate sequence of any of SEQ ID Nos.: 12–15.

3. A method for detecting and differentiating an enterovirus in a sample, comprising:
a) contacting nucleic acids in the sample with a pair of primers to form an amplification product, wherein a first primer of said pair consists of a sequence of any of SEQ ID NOs: 1–5 or a degenerate sequence of SEQ ID NO: 5, and a second primer of said pair consists of a sequence of any of SEQ ID NOs: 6–8 or a degenerate sequence of SEQ ID NO: 8, provided that the second primer consists of the sequence of SEQ ID No: 8 or a degenerate sequence of SEQ ID No: 8 when the first primer consists of the sequence of SEQ ID NO: 5 or a degenerate sequence of SEQ ID NO: 5; and
b) contacting the amplification product generated in step a) with at least one synthetic nucleotide sequence fixed on a solid substrate, wherein the synthetic nucleotide sequence comprises any sequence selected from the group consisting of SEQ ID NOs: 9–15 or a degenerate sequence of any of SEQ ID NOs: 12–15, and detecting hybridization, thereby detecting and differentiating an enterovirus in the sample.

4. A method for detecting and differentiating an enterovirus in a sample comprising contacting nucleic acids in a sample with at least one synthetic nucleotide sequence fixed on a solid substrate, wherein the synthetic nucleotide sequence comprises any sequence selected from the group consisting of SEQ ID NOs: 9–15, or a degenerate sequence of SEQ ID NOs: 12–15 and detecting hybridization, thereby detecting and differentiating an enterovirus in the sample.

* * * * *

SEQUENCE LISTING

<160> NUMBER OF SEQ ID NOS: 16

<210> SEQ ID NO 1
<211> LENGTH: 16
<212> TYPE: DNA
<213> ORGANISM: Artificial Sequence
<220> FEATURE:
<223> OTHER INFORMATION: Artificial Sequence is Synthesized

<400> SEQUENCE: 1
ttgtrcgcct gtttta                                                      16

<210> SEQ ID NO 2
<211> LENGTH: 21
<212> TYPE: DNA
<213> ORGANISM: Artificial Sequence
<220> FEATURE:
<223> OTHER INFORMATION: Artificial Sequence is Synthesized

<400> SEQUENCE: 2
caagcacttc tgthhccccg g                                                21

<210> SEQ ID NO 3
<211> LENGTH: 19
<212> TYPE: DNA
<213> ORGANISM: Artificial Sequence
<220> FEATURE:
<223> OTHER INFORMATION: Artificial Sequence is Synthesized

<400> SEQUENCE: 3
tacttcgaga arccyagta                                                   19

<210> SEQ ID NO 4
<211> LENGTH: 17
<212> TYPE: DNA
<213> ORGANISM: Artificial Sequence
<220> FEATURE:
<223> OTHER INFORMATION: Artificial Sequence is Synthesized

<400> SEQUENCE: 4
aagagyctat tgagcta                                                     17

<210> SEQ ID NO 5
<211> LENGTH: 20
<212> TYPE: DNA
<213> ORGANISM: Artificial Sequence
<220> FEATURE:
<223> OTHER INFORMATION: Artificial Sequence is Synthesized
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (18)..(18)
<223> OTHER INFORMATION: n = inosine

<400> SEQUENCE: 5
ggntggtrst ggaarttncc                                                  20

<210> SEQ ID NO 6
<211> LENGTH: 19
<212> TYPE: DNA
<213> ORGANISM: Artificial Sequence
<220> FEATURE:
<223> OTHER INFORMATION: Artificial Sequence is Synthesized

```
<400> SEQUENCE: 6
cacyggatgg ccaatccaa                                          19

<210> SEQ ID NO 7
<211> LENGTH: 20
<212> TYPE: DNA
<213> ORGANISM: Artificial Sequence
<220> FEATURE:
<223> OTHER INFORMATION: Artificial Sequence is Synthesized

<400> SEQUENCE: 7
attgtcacca taagcagcca                                         20

<210> SEQ ID NO 8
<211> LENGTH: 20
<212> TYPE: DNA
<213> ORGANISM: Artificial Sequence
<220> FEATURE:
<223> OTHER INFORMATION: Artificial Sequence is Synthesized
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (18)..(18)
<223> OTHER INFORMATION: n = inosine

<400> SEQUENCE: 8
arrttnatcc aytgrtgngg                                         20

<210> SEQ ID NO 9
<211> LENGTH: 27
<212> TYPE: DNA
<213> ORGANISM: Artificial Sequence
<220> FEATURE:
<223> OTHER INFORMATION: Artificial Sequence is Synthesized

<400> SEQUENCE: 9
tcctccggcc cctgaatgcg gctaatc                                 27

<210> SEQ ID NO 10
<211> LENGTH: 33
<212> TYPE: DNA
<213> ORGANISM: Artificial Sequence
<220> FEATURE:
<223> OTHER INFORMATION: Artificial Sequence is Synthesized

<400> SEQUENCE: 10
tgtcgtaacg sgcaastcyg yrgcggaacc gac                          33

<210> SEQ ID NO 11
<211> LENGTH: 28
<212> TYPE: DNA
<213> ORGANISM: Artificial Sequence
<220> FEATURE:
<223> OTHER INFORMATION: Artificial Sequence is Synthesized

<400> SEQUENCE: 11
tactttgggt gtccgtgttt chttttat                                28

<210> SEQ ID NO 12
<211> LENGTH: 30
<212> TYPE: DNA
<213> ORGANISM: Artificial Sequence
<220> FEATURE:
```

-continued

```
<223> OTHER INFORMATION: Artificial Sequence is Synthesized

<400> SEQUENCE: 12
cttataagca gactcaaccc ggtgctgatg                                30

<210> SEQ ID NO 13
<211> LENGTH: 28
<212> TYPE: DNA
<213> ORGANISM: Artificial Sequence
<220> FEATURE:
<223> OTHER INFORMATION: Artificial Sequence is Synthesized

<400> SEQUENCE: 13
tggcattcca atatcacaat taacagtg                                  28

<210> SEQ ID NO 14
<211> LENGTH: 30
<212> TYPE: DNA
<213> ORGANISM: Artificial Sequence
<220> FEATURE:
<223> OTHER INFORMATION: Artificial Sequence is Synthesized

<400> SEQUENCE: 14
ctcggcacta tcgcaggagg gaccgggaat                                30

<210> SEQ ID NO 15
<211> LENGTH: 30
<212> TYPE: DNA
<213> ORGANISM: Artificial Sequence
<220> FEATURE:
<223> OTHER INFORMATION: Artificial Sequence is Synthesized

<400> SEQUENCE: 15
cctacgccac tacacagcct ggtcaggttg                                30

<210> SEQ ID NO 16
<211> LENGTH: 1560
<212> TYPE: DNA
<213> ORGANISM: Enterovirus 71

<400> SEQUENCE: 16
ttaaaacagc tgtgggttgt cacccaccca cagggtccac tgggcgctag tacactggta    60
tctcggtacc tttgtacgcc tgttttatac cccctccctg atttgcaact tagaagcaac   120
gcaaaccaga tcaatagtag gtgtgacata ccagtcgcat cttgatcaag cacttctgta   180
tccccggacc gagtatcaat agactgtgca cacggttgaa ggagaaaacg tccgttaccc   240
ggctaactac ttcgagaagc ctagtaacgc cattgaagtt gcagagtgtt tcgctcagca   300 ctcccccgt gtagatcagg tcgatgagtc accgcattcc ccacgggcga ccgtggcggt   360
ggctgcgttg gcggcctgcc tatggggtaa cccataggac gctctaatac ggacatggcg   420
tgaagagtct attgagctag ttagtagtcc tccggcccct gaatgcggct aatcctaact   480
gcggagcaca tacccttaat ccaaagggca gtgtgtcgta acgggcaact ctgcagcgga   540
accgactact ttgggtgtcc gtgtttcttt ttattcttgt attggctgct tatggtgaca   600
attaaagaat tgttaccata tagctattgg attggccatc cagtgtcaaa cagagctatt   660
gtatatctct tgttggatt cacacctctc actcttgaaa cgttacacac cctcaattac   720
attatactgc tgaacacgaa gcgatgggct cccaggtctc cacacagcga tccggctcgc   780
atgagaattc caactcagcc acggaaggct ccactataaa ttacacaacc attaattact   840
acaaagactc gtatgctgcc actgctggaa agcaaagtct caaacaagat cctgacaagt   900
```

```
ttgcgaaccc tgtgaaggac atctttactg aaatggcagc gcccttaaag tctccctctg    960
ctgaagcatg tggctatagc gaccgagtgg cacagcttac cattggaaat tccaccatta   1020
ctacacaaga agcagcaaac ataatagttg ggtatggtga gtggccttca tactgctctg   1080
ataatgatgc aacagcggta gacaaaccta cacggcctga tgtctcagta aatagatttt   1140
acacgctaga cactaagcta tgggagaaat catccaaggg gtggtactgg aagttcccag   1200
atgtactgac tgaaaccgga gtttttggtc caaatgcaca atttcactac ttataccgtt   1260
cagggttctg catccacgtt caatgtaacg ctagcaaatt tcaccaaggg gcgctactcg   1320
ttgcggtatt gcccgagtat gtcattggaa cagtggcagg cggcacaggc acagagaaca   1380
gtcaccctcc ttataaacaa acccaacccg gcgctgatgg atttgaatta caacatccat   1440
atgttcttga tgctggaatt ccaatatctc agttgacagt gtgccctcac cagtggatca   1500
atttacgaac caacaattgt gccaccataa tagtgccata catgaacaca ctaccttttg   1560
```